United States Patent
Devassine et al.

(10) Patent No.: US 11,833,239 B2
(45) Date of Patent: Dec. 5, 2023

(54) ANHYDROUS SILKY COSMETIC PRODUCT

(71) Applicant: AKI, Inc., Chattanooga, TN (US)

(72) Inventors: Mickael Devassine, Ooltewah, TN (US); Hrazhyhna Devassine, Ooltewah, TN (US)

(73) Assignee: AKI, Inc., Chattanooga, TN (US)

( * ) Notice: Subject to any disclaimer, the term of this patent is extended or adjusted under 35 U.S.C. 154(b) by 241 days.

(21) Appl. No.: 17/228,167

(22) Filed: Apr. 12, 2021

(65) Prior Publication Data

US 2021/0315795 A1    Oct. 14, 2021

Related U.S. Application Data

(60) Provisional application No. 63/009,187, filed on Apr. 13, 2020.

(51) Int. Cl.

| | |
|---|---|
| *A61K 8/891* | (2006.01) |
| *A61K 8/04* | (2006.01) |
| *A61K 8/92* | (2006.01) |
| *A61K 8/31* | (2006.01) |
| *A61Q 13/00* | (2006.01) |
| *A61Q 1/00* | (2006.01) |
| *A61K 8/37* | (2006.01) |
| *A61K 8/49* | (2006.01) |
| *A61Q 19/00* | (2006.01) |

(52) U.S. Cl.
CPC .............. *A61K 8/891* (2013.01); *A61K 8/042* (2013.01); *A61K 8/31* (2013.01); *A61K 8/37* (2013.01); *A61K 8/4953* (2013.01); *A61K 8/922* (2013.01); *A61Q 13/00* (2013.01); *A61Q 19/00* (2013.01); *A61K 2800/10* (2013.01); *A61K 2800/31* (2013.01); *A61K 2800/43* (2013.01); *A61K 2800/524* (2013.01); *A61K 2800/591* (2013.01)

(58) Field of Classification Search
None
See application file for complete search history.

(56) References Cited

U.S. PATENT DOCUMENTS

| | | | | |
|---|---|---|---|---|
| 6,248,339 | B1* | 6/2001 | Knitowski | A61K 8/891 |
| | | | | 512/1 |
| 9,233,061 | B2* | 1/2016 | Jang | A61Q 19/00 |
| 9,526,738 | B2 | 12/2016 | Stasko | |
| 2008/0085961 | A1* | 4/2008 | Lin | C08L 53/02 |
| | | | | 524/487 |
| 2008/0206172 | A1 | 8/2008 | Mohammadi | |
| 2009/0214458 | A1 | 8/2009 | Brun | |
| 2013/0344121 | A1 | 12/2013 | Kim | |
| 2016/0250137 | A1 | 9/2016 | Noor | |

FOREIGN PATENT DOCUMENTS

| | | |
|---|---|---|
| DE | 102013223789 A1 | 4/2014 |
| WO | 2012098116 A1 | 7/2012 |
| WO | 2019096954 A1 | 5/2019 |

OTHER PUBLICATIONS

Written Opinion of the International Searching Authority, International Application No. PCT/US2021/026921, dated Jul. 8, 2021.
Lachenmeier, DW. Safety evaluation of topical applications of ethanol on the skin and inside the oral cavity. J Occup Med Toxicol. Nov. 13, 2008;3:26. doi: 10.1186/1745-6673-3-26. PMID: 19014531; PMCID: PMC2596158.

* cited by examiner

*Primary Examiner* — Dominic Lazaro
(74) *Attorney, Agent, or Firm* — Rivkin Radler LLP

(57) ABSTRACT

An anhydrous and alcohol-free cosmetic product having a silky feel containing: 10 to 99, preferably 40 to 90, percent by weight dimethicone crosspolymer gel dispersed in a non-silicone fluid; and 1 to 30 percent by weight lipophilic actives, fragrance oils, or a combination thereof. The product can also contain 1 to 90 percent by weight non-silicone fluid to adjust the viscosity. This solvent can be volatile to produce a dry feel on the skin. One or more emollients can be used to moisturize the skin or to increase the miscibility of the actives and fragrance. Moreover, a preservative and some pigments can be added to the formula to preserve the product from bacteria contamination and to improve the aesthetics. The product can be used with a variety of cosmetic or fragrance products such as creams, gels, and lotions.

17 Claims, No Drawings

ANHYDROUS SILKY COSMETIC PRODUCT

CROSS REFERENCE TO RELATED APPLICATIONS

This application claims priority to U.S. Provisional Application Ser. No. 63/009,187, filed Apr. 13, 2020, the contents of which are incorporated herein by reference in its entirety.

FIELD OF THE APPLICATION

The disclosed subject matter relates to an anhydrous silky cosmetic product containing dimethicone crosspolymer gel dispersed in a non-silicone fluid that has a silky feel when applied to the skin.

DESCRIPTION OF THE RELATED ART

Alcohols such as ethanol are commonly used as solvents in the cosmetics industry, especially for fragrances such as perfumes, colognes, and aftershaves. Alcohol, however, has well-known deleterious effects, such as drying and irritation of the skin, skin diseases, and low lasting of the fragrance due to the rapid evaporation of odorous molecules caused by evaporation of the ethanol. Thus, there is a need for non-alcoholic cosmetic formulations that avoid the negative effects of ethanol while maintaining the benefits of fragrance lift from the skin. Furthermore, many consumers enjoy cosmetic products with a pleasant, silky texture and good clarity. The use of a volatile solvent can bring a dry feel of the formulation. Thus, the use of crosspolymers has been investigated.

U.S. Pat. App. Pub. No. 20090214458 to Brun et al. describes a composition to treat keratin fibers comprising at least one copolymers based on silicone resin and fluid silicone, at least one volatile solvent, and at least one silicone resins containing at least one trifunctional unit of formula $(CH_3)SiO_{3/2}$.

U.S. Pat. No. 6,248,339 to Knitowski et al. discloses a fragrant body lotion or cream, which utilizes a cyclomethicone/dimethicone crosspolymer gel which contains a volatile cyclic fluid and a fragrance oil.

U.S. Pat. App. Pub. No. 20080206172 to Mohammadi et al. relates clear sunscreen gels, which contain chemical ultra-violet light absorber, one silicone solvent such as dimethicone and a diphenyl silicone elastomer gellant.

U.S. Pat. No. 9,526,738 to Stasko et al. relates to non-aqueous topical gels for the treatment of wounds and other skin ailments. These gels comprise diazeniumdiolate-functionalized polysiloxane macromolecules at a concentration in range of 0.1 to 20 weight %, a cyclic silicone fluid (cyclomethicone) at a concentration in a range of 5 to 30 weight % and crosslinked polydimethylsiloxane at a concentration in a range of 65 to 85 weight %.

While there are known cosmetic products containing crosspolymers, there remains a need for an anhydrous silky cosmetic product containing dimethicone crosspolymer gel dispersed in a non-silicone fluid that has a silky feel when applied to the skin.

SUMMARY

The purpose and advantages of the disclosed subject matter are set forth in the following description, and additional advantages may be obtained by the practice and knowledge of those skilled in the art based on this description.

The disclosed subject matter provides, according to some embodiments, an anhydrous and alcohol-free cosmetic product having a silky feel. The anhydrous silky cosmetic product contains 10 to 99, preferably 40 to 90, percent by weight dimethicone crosspolymer gel dispersed in a non-silicone fluid; and 1 to 30 percent by weight of lipophilic active(s), fragrance oil, or a combination thereof. Embodiments also contain 1 to 90 percent by weight non-silicone fluid to adjust the viscosity. In embodiments, this solvent can be volatile to produce a dry feel on the skin. In other embodiments, emollients can be used to moisturize the skin or to increase the miscibility of the actives and fragrance. Moreover, a preservative and some pigments can be added to the anhydrous silky cosmetic product to preserve the product from bacteria contamination and to improve the aesthetics. The anhydrous silky cosmetic product can be used with a variety of cosmetic or fragrance products such as creams, gels, and lotions. In the case of a fragrance product, the absence of alcohol allows to increase the fragrance lasting and avoid a drying of skin.

The foregoing summary and the following detailed description are exemplary and are intended to provide an explanation of the disclosed subject matter.

DETAILED DESCRIPTION

The anhydrous silky cosmetic product presented herein may be employed by a user to obtain the benefits of the cosmetic product without the disadvantages associated with using alcohol as a solvent in such products. The disclosed subject matter is particularly suited for use with creams, gels, lotions, and the like, especially for users with sensitive skin.

For purpose of explanation and illustration, and not limitation, exemplary embodiments of the anhydrous silky cosmetic product in accordance with the disclosed subject matter are described herein.

The disclosed subject matter relates to an anhydrous silky cosmetic product containing dimethicone crosspolymer gel dispersed in a non-silicone fluid that has a silky feel when applied to the skin. (The term "cosmetic" is used throughout this application to refer to any compound, composition, product, and the like that is intended to be applied to a person's body to improve the person's appearance, fragrance, attractiveness, and the like. This includes, without limitation, makeup, creams, gels, fragrances such as perfume, cologne, aftershaves, and the like.)

In accordance with the disclosed subject matter, the crosspolymer dispersed in a non-silicone fluid creates a barrier to let the active or the fragrance adhere to the skin, help to maintain moisture of the skin and brings a silky effect on skin. The use of a volatile non-silicone solvent may be added to avoid an oily feel on the skin because of its quick evaporation. In the case of a fragrance composition such as a fragrance gel, the use of a non-silicone volatile solvent will improve fragrance lift from the skin without alcohol flash, while maintaining a dry feel.

In accordance with the disclosed subject matter, as embodied and broadly described herein, the anhydrous silky cosmetic product is preferably composed of: 10 to 99, preferably 40 to 90, percent by weight dimethicone crosspolymer gel dispersed in a non-silicone fluid (alternatively 45 to 82.5 percent by weight, 65 to 70 percent by weight); and 1 to 30 percent by weight lipophilic active(s), fragrance oil, or a combination thereof. In embodiments, the product can also contain 1 to 90 percent by weight non-silicone fluid to adjust the viscosity. In embodiments, this solvent can be volatile to produce a dry feel on the skin.

In embodiments of the anhydrous silky cosmetic product, the composition includes one or more lipophilic actives such as anti-aging, anti-wrinkle, vitamins, sunscreen, anti-acne ingredients, and fragrance.

In embodiments, one or more emollients can be used to moisturize the skin or to increase the miscibility of the actives and fragrance in other embodiments. Moreover, in some embodiments, a preservative and some pigments can be added to the formula to preserve the product from bacteria contamination and to improve the aesthetics. The anhydrous silky cosmetic product, in accordance with the disclosed subject matter, can be used with a variety of cosmetic or fragrance products such as creams, gels, and lotions.

The disclosed subject matter allows the anhydrous silky cosmetic product to contain no alcohol or water. Therefore, in some embodiments, the addition of about 1 to 90 percent by weight non-silicone fluid can be used to adjust the viscosity and, when a volatile fluid is used, to get a dry feel. Furthermore, in some embodiments, one or more emollients can be added to the anhydrous silky cosmetic product to increase the miscibility of the active or fragrance oil, to keep the skin moist and flexible, or to help to prevent cracks.

Embodiments of the anhydrous silky cosmetic product contain at least one dimethicone crosspolymer gel composed of a silicone crosspolymer (generally between 8 to 12 percent in weight) dispersed in a non-silicone fluid, volatile or non-volatile. Examples of suitable dimethicone crosspolymers gels in accordance with the disclosed subject matter include dodecane/dimethicone crosspolymer, isododecane/dimethicone crosspolymer, dodecane/vinyl dimethicone crosspolymer, isododecane/vinyl dimethicone crosspolymer, dodecane/cetearyl dimethicone crosspolymer, tetradecane/dimethicone crosspolymer and isododecane/cetearyl dimethicone crosspolymer. Inclusion of a suitable dimethicone crosspolymer gel in the anhydrous silky cosmetic product allows the active or fragrance to adhere to the skin and helps to maintain the moisture of the skin by creating a barrier. Furthermore, the silicone crosspolymer lends the anhydrous silky cosmetic product a silky feel.

In embodiments, the dimethicone crosspolymer gel can be dispersed in a non-silicone medium, which can be volatile or non-volatile. In some embodiments, this non-silicone fluid preferably comprises a vegetable oil such as isopropyl myristate or isopropyl palmitate.

In certain embodiments of the anhydrous silky cosmetic product, addition of about 1 to 90 percent by weight non-silicone fluid can adjust the viscosity and, when a volatile fluid is used, obtain a dry feel. This non-silicone fluid can comprise one or more liquids that allow the viscosity to be adjusted and, when a volatile fluid is used, help achieve a dry effect on the skin due to quick evaporation. Examples of such non-silicone and volatile dispersion fluids are preferably volatile hydrocarbon oils such as volatile hydrocarbon oils having from 8 to 16 carbon atoms and mixtures thereof, and branched alkanes, $C_8$-$C_{16}$ isoalkanes (also called isoparaffins) $C_8$-$C_{16}$, isododecane, isodecane and for example the oils sold under the trade names Isopar or Permethyl, and mixtures thereof. The hydrocarbon oils can be naturally derived vegetable alkanes from renewable sources such as coconut alkanes. Other examples of volatile non-silicone fluids include volatile glycols ether, perfluoroalkanes $C_4$-$C_{10}$, perfluorocycloalkyls, perfluorocycloalkyls, ethers, hydrogenated polyalkenes (Dedraflow 5), esters (coco caprylate/caprate), etc. In embodiments, the volatile non-silicone dispersion fluid is the dispersion media of the dimethicone crosspolymer. The volatility of that fluid leads to a dry effect on the skin due to its quick evaporation.

In other embodiments, in the case of a fragrance product, dipropylene glycol, Hedione or isopropyl myristate or isopropyl palmitate or triethyl citrate or benzyl benzoate are generally the diluents used to make fragrance. Dipropylene glycol and triethyl citrate are diluents more polar than the others.

In embodiments, an emollient can be added to the anhydrous silky cosmetic product to moisturize the skin or to increase the miscibility of the active or fragrance product, for example, when a high level of non-silicone volatile fluid is used in the formulation. Examples of suitable emollients are isononyl isononanoate, Aloe Vera, PPG-20 methyl glucose ether distearate, caprylic/capric triglyceride, neopentyl glycol diheptanoate, jojoba oil, isopropyl isostearate, and polyisobutene.

Additionally, in some embodiments, one or more preservatives, pigments, or combinations thereof, can be added to the anhydrous silky cosmetic product to preserve the product from bacteria contamination and to improve the aesthetics.

The viscosity range of the anhydrous silky cosmetic product is about 1 to 200,000 cps.

Exemplary embodiments of the anhydrous silky cosmetic product in accordance with the present disclosure will now be described.

Example 1

Table 1 lists the ingredients and composition of an anhydrous silky cosmetic product in accordance with the present disclosure. Example 1 is a highly viscous fragrance gel that is clear and sparkly.

TABLE 1

| INGREDIENTS | PREFERRED WEIGHT % | RANGE IN WEIGHT % |
| --- | --- | --- |
| Oleosil T (Tetradecane (and) Dimethicone Crosspolymer-3) | 82.5 | 10-99 |
| Fragrance | 17.4 | 1-30 |
| Glamour CF Deep Pink | 0.1 | 0-5 |

Example 2

Table 2 lists the ingredients and composition of an anhydrous silky cosmetic product in accordance with the present disclosure. Example 2 is a highly viscous fragrance gel that is clear and sparkly.

TABLE 2

| INGREDIENTS | PREFERRED WEIGHT % | RANGE IN WEIGHT % |
| --- | --- | --- |
| BeauSil Gel 8071 (C13-15 Alkane (and) Isododecane (and) Dimethicone/Vinyl Dimethicone Crosspolymer) | 65 | 10-99 |
| Isododecane | 17.5 | 1-90 |
| Fragrance | 17.4 | 1-30 |
| Glamour CF Flashy Pink | 0.1 | 0-5 |

Example 3

Table 3 lists the ingredients and composition of an anhydrous silky cosmetic product in accordance with the present disclosure. Example 3 is a highly viscous anti-aging gel.

TABLE 3

| INGREDIENTS | PREFERRED WEIGHT % | RANGE IN WEIGHT % |
|---|---|---|
| BeauSil Gel 8071 (C13-15 Alkane (and) Isododecane (and) Dimethicone/Vinyl Dimethicone Crosspolymer) | 65.0 | 10-99 |
| Isododecane | 20.0 | 1-90 |
| Isononyl Isononanoate | 13.0 | 0-30 |
| Gatuline In-tense | 2.0 | 1-2 |

Example 4

Table 4 lists the ingredients and composition of an anhydrous silky cosmetic product in accordance with the present disclosure. Example 4 is a medium-viscosity antiperspirant foot cream.

TABLE 4

| INGREDIENTS | PREFERRED WEIGHT % | RANGE IN WEIHT % |
|---|---|---|
| BeauSil Gel 8071 (C13-15 Alkane (and) Isododecane (and) Dimethicone/Vinyl Dimethicone Crosspolymer) Isododecane | 45 | 10-99 |
| Reach 301 | 34 | 1-90 |
| Rose Talc | 15 | 5-20 |
| Menthyl PCA (and) Menthol (and) Dipropylene Glycol | 5 | 1-10 |
|  | 1 | 0-2 |

Example 5

Table 5 lists the ingredients and composition of an anhydrous silky cosmetic product in accordance with the present disclosure. Example 5 is an anti-cellulite cream.

TABLE 5

| INGREDIENTS | PREFERRED WEIGHT % | RANGE IN WEIGHT % |
|---|---|---|
| BeauSil Gel 8071 (C13-15 Alkane (and) Isododecane (and) Dimethicone/Vinyl Dimethicone Crosspolymer) | 70.0 | 10-99 |
| Isododecane | 16.5 | 1-90 |
| Isononyl Isononanoate | 12.75 | 0-30 |
| Fragrance | 0.5 | 0-20 |
| Caffeine | 0.25 | 0.1-0.25 |

Table 6 indicates the ingredients and composition of gels obtained with a crosspolymer (Dimethicone Crosspolymer-3), a volatile fluid (dodecane) and fragrance diluents, in accordance with the present disclosure.

TABLE 6

| DILUENT NAME | DILUENT WEIGHT % | OLEOSIL D WEIGHT % | DODECANE WEIGHT % | RESULTS |
|---|---|---|---|---|
| HEDIONE | 5 | 80 | 15 | Highly viscous gel |
|  | 10 | 80 | 10 | Highly viscous gel |
|  | 20 | 80 | — | Highly viscous gel |
| BENZYL BENZOATE | 5 | 80 | 15 | Highly viscous gel |
|  | 10 | 80 | 10 | Highly viscous gel |
|  | 20 | 80 | — | Highly viscous gel |
| ISOPROPYL-MYRISTATE | 5 | 80 | 15 | Highly viscous gel |
|  | 10 | 80 | 10 | Highly viscous gel |
|  | 20 | 80 | — | Highly viscous gel |
| DIPROPYLENE GLYCOL | 5 | 80 | 15 | Non-miscible |
|  | 10 | 80 | 10 | Non-miscible |
|  | 20 | 80 | — | Non-miscible |
| TRIETHYL CITRATE | 5 | 80 | 15 | Non-miscible |
|  | 10 | 80 | 10 | Non-miscible |
|  | 20 | 80 | — | Non-miscible |

The foregoing description of exemplary embodiments, including examples, is presented only to describe, explain, and illustrate the broad concepts of the disclosed subject matter, and is not intended and should not be construed to limit the scope of the of the present disclosure. Various modifications and improvements may be made by those skilled in the art without departing from the scope. Thus, the disclosed subject matter includes all modifications and improvements that are within the scope of the following claims and their equivalents.

What is claimed is:

1. An anhydrous silky cosmetic product including:
   an anhydrous dimethicone crosspolymer gel dispersed in a first non-silicone fluid, in an amount of 10 to 99 percent by weight; and
   at least one lipophilic active, in an amount of 1 to 30 percent by weight, wherein the anhydrous silky cosmetic product does not contain a silicone fluid.

2. The anhydrous silky cosmetic product of claim 1, further comprising:
   a second non-silicone fluid, in an amount of 1 to 90 percent by weight;
   wherein the anhydrous dimethicone crosspolymer gel is in an amount of 10 to 98 percent by weight.

3. The anhydrous silky cosmetic product of claim 2, wherein the second non-silicone fluid comprises a volatile hydrocarbon oil.

4. The anhydrous silky cosmetic product of claim 3, where in the volatile hydrocarbon oil comprises 8 to 16 carbon atoms per molecule.

5. The anhydrous silky cosmetic product of claim 3, where in the volatile hydrocarbon oil comprises a branched alkane $C_8$-$C_{16}$, an isoalkane $C_8$-$C_{16}$, isododecane, isodecane, a vegetable derived alkane, a volatile glycol ether, a perfluoroalkane $C_4$-$C_{10}$, a perfluorocycloalkyl, a perfluorocycloalkyl, an ether, a hydrogenated polyalkene, or an ester.

6. The anhydrous silky cosmetic product of claim 1, wherein the lipophilic active comprises an anti-aging ingredient, an anti-wrinkle ingredient, a vitamin, a sunscreen, an anti-acne ingredient, or a fragrance oil.

7. The anhydrous silky cosmetic product of claim 1, further comprising at least one emollient.

8. The anhydrous silky cosmetic product of claim 7, where in the emollient comprises isononyl isononanoate, Aloe Vera, polypropylene glycol-20 methyl glucose ether distearate (PPG-20 methyl glucose ether distearate), caprylic/capric triglyceride, neopentyl glycol diheptanoate, jojoba oil, isopropyl isostearate, or polyisobutene.

9. The anhydrous silky cosmetic product of claim 1, wherein the anhydrous dimethicone crosspolymer comprises dodecane/dimethicone crosspolymer, isododecane/dimethicone crosspolymer, dodecane/vinyl dimethicone crosspolymer, isododecane/vinyl dimethicone crosspolymer, dodecane/cetearyl dimethicone crosspolymer, tetradecane/dimethicone crosspolymer, or isododecane/cetearyl dimethicone crosspolymer.

10. The anhydrous silky cosmetic product of claim 1, wherein, the first non-silicone fluid comprises a vegetable oil.

11. The anhydrous silky cosmetic product of claim 10, wherein the vegetable oil comprises isopropyl myristate or isopropyl palmitate.

12. The anhydrous silky cosmetic product of claim 1, further comprising a preservative.

13. The anhydrous silky cosmetic product of claim 1, further comprising a pigment.

14. The anhydrous silky cosmetic product of claim 1, wherein the anhydrous dimethicone crosspolymer gel is in an amount of 40 to 90 percent by weight.

15. The anhydrous silky cosmetic product of claim 1, wherein the anhydrous dimethicone crosspolymer gel is in an amount of 45 to 82.5 percent by weight.

16. The anhydrous silky cosmetic product of claim 1, wherein the anhydrous dimethicone crosspolymer gel is in an amount of 65 to 70 percent by weight.

17. The anhydrous silky cosmetic product of claim 1, further comprising caffeine.

\* \* \* \* \*